United States Patent [19]

Beard

[11] Patent Number: 4,485,810
[45] Date of Patent: Dec. 4, 1984

[54] SURGICAL CUTTING BLADE
[75] Inventor: Robert Beard, Placerville, Calif.
[73] Assignee: Oximetrix, Inc., Mountain View, Calif.
[21] Appl. No.: 201,603
[22] Filed: Oct. 28, 1980
[51] Int. Cl.³ .............................................. A61B 17/32
[52] U.S. Cl. .................................... 128/303.1; 30/140
[58] Field of Search ........... 128/303.1, 303.17, 303 R, 128/303.12; 30/140, 128

[56] References Cited

U.S. PATENT DOCUMENTS

| | | | |
|---|---|---|---|
| 2,297,103 | 9/1942 | Holm | 30/140 |
| 2,866,068 | 12/1958 | Bernstein et al. | 30/140 |
| 3,685,518 | 8/1972 | Beuerle et al. | 128/303.17 |
| 4,198,957 | 4/1980 | Cage | 128/303.1 |

FOREIGN PATENT DOCUMENTS 2315075  12/1974  Fed. Rep. of Germany ... 128/303.1

OTHER PUBLICATIONS

"Chem. Engr. Handbook", McGraw Hill, 5th Ed., Properties of Materials, Table 23-5.

Primary Examiner—Benjamin R. Padgett
Assistant Examiner—T. J. Wallen
Attorney, Agent, or Firm—Robert S. Kelly

[57] ABSTRACT

The cutting instrument of this invention is adapted to be heated to a predetermined temperature range and includes a steel substrate having a cutting edge, a copper composition having a yield strength of at least 25,000 p.s.i. laminated to the steel substrate and an electrical heater means secured to the copper composition laminate. The cutting edge of the cutting instrument and at least a part of the copper composition and heater means may be coated with a non-stick composition in order to prevent the cutting instrument from sticking to the subject upon which the cutting operation is performed with the cutting instrument.

5 Claims, 4 Drawing Figures

SURGICAL CUTTING BLADE

BACKGROUND OF THE INVENTION

The control of bleeding during surgery accounts for a major portion of the total time involved in a surgical operation. When tissue is incised, the attendant bleeding obscures the surgeon's vision, reduces his surgical precision and often dictates slow and elaborate procedures in surgical operation. Typically, each bleeding vessel must be grasped in a surgical clamp in order to stop the flow of blood and the tissue and vessel within each clamp are then tied with pieces of fine thread. Such ligated masses of tissue subsequently die and decompose thus tending to retard healing and provide a possible site for infection. A substantial amount of effort with regard to the heating of a cutting instrument so as to provide simultaneous hemostatis has been conducted by Robert F. Shaw and patents related to such efforts include U.S. Pat. No. Re 29,088 which issued on Jan. 11, 1977, U.S. Pat. No. Re 30,190 which issued on Jan. 15, 1980, U.S. Pat. No. 4,089,836 which issued on May 16, 1978, U.S. Pat. No. 4,091,813 which issued on May 30, 1978, U.S. Pat. No. 4,185,632 which issued on Jan. 29, 1980, and U.S. Pat. No. 4,207,896 which issued on June 17, 1980.

DESCRIPTION OF PREFERRED EMBODIMENTS

Figure 1:
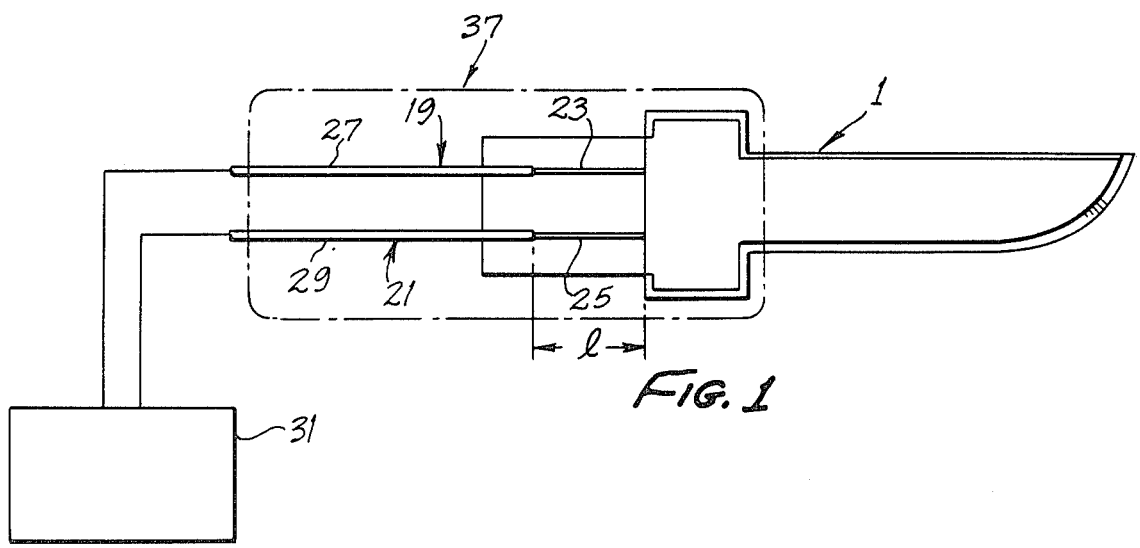
FIG. 1 is a pictorial view illustrating the subject matter of this invention.

Referring now to FIG. 1 of the drawings, there is shown a cutting instrument 1 including a steel substrate 3. A copper composition 5 having a yield strength of at least 25,000 p.s.i. is laminated to the steel substrate 3. The copper composition 5 is preferably an alumina dispersion strengthened copper wherein the alumina present in the copper composition is from between about 0.1 and about 0.5 percent by weight of the total composition. Preferably the alumina-copper dispersion is of the type referred to and sold commercially as Glidcop by the Glidden Company. The steel substrate 3 and copper composition laminate 5 should be capable of experiencing a heat treatment at least to a temperature of approximately 1500 degrees F.

A heater means 7, preferably formed of copper in a strip having a generally tortuous or serpentine shape substantially uniformly distributed along the copper composition 5, is secured to the copper composition laminate 5 by means of an adhesive 35 that includes an electrically insulative and thermally conductive filler material 13 admixed with a material selected from a group consisting of polyimide, polyamide, phenolic, silicone, acrylic and epoxy resins 15. The electrically insulative properties of the filler material 13 is preferably at least 100 K ohms while the thermal conductivity properties of the filler material 13 is preferably defined as having a heat flow per unit of temperature of a least 0.1 watts per degree centigrade. In one embodiment, the diameter of such filler material 13 is such that the material spans the distance between the heater means 7 and the copper composition 5 thereby serving as the spacing means for the heater means and providing the optimum thermal transfer between the heater means 7 and the copper composition 5.

The steel substrate 3 includes a cutting edge 17 which is preferably coated with a non-stick means 9 in order to preclude the cutting edge from sticking to a subject upon which a cutting operation is performed. Further, at least a portion of the balance of the cutting instrument is also similarly coated by non-stick means 11. Preferably the non-stick means 9 applied to the cutting edge 17 is a dispersion of fluorocarbon particles within a silicone adhesive binder while the non-stick means applied to the balance of the cutting instrument is a fluorocarbon composition. The non-stick means 9 and 11 are preferably a form of polytetrafluoroethylene and chosen from the group consisting of tetrafluoroethylene, polyfluorinated alcoxy abd fluoroinated ethylene polymer.

At least a pair of electrical leads 19 and 21 are provided for incoming and outgoing current flow to the heater means 7. Such electrical leads 19 and 21 include non-insulated portions 23 and 25 and insulated portions 27 and 29, respectively, connecting the heater means 7 to an external power source 31. In a preferred embodiment, a electrically insulative polyimide 33 backing material is provided upon which the heater 7 and adhesive 35 may be disposed prior to being secured to the copper composition 5.

The structure of the present invention having been described, its method of operation will now be discussed. Upon application of electrical current from the external power source 31 through the pair of electrical leads 19 and 21 heater means 7 is heated and heat is thermally conducted through the adhesive 35 to the copper composition 5 and the steel substrate 3 with its cutting edge 17. Such heat transfer from the heater means 7 to the steel substrate 3 is carried out in accordance with the heat transfer equation $q = K\ a(\text{delta } T/\text{delta } x)$ where q is the amount of heat transferred, K is the thermal heat transfer coefficient, a is the area through which the heat is transferred, delta T is the differential temperature and delta x is the thickness of the material through which the heat is transferred.

Figure 4:
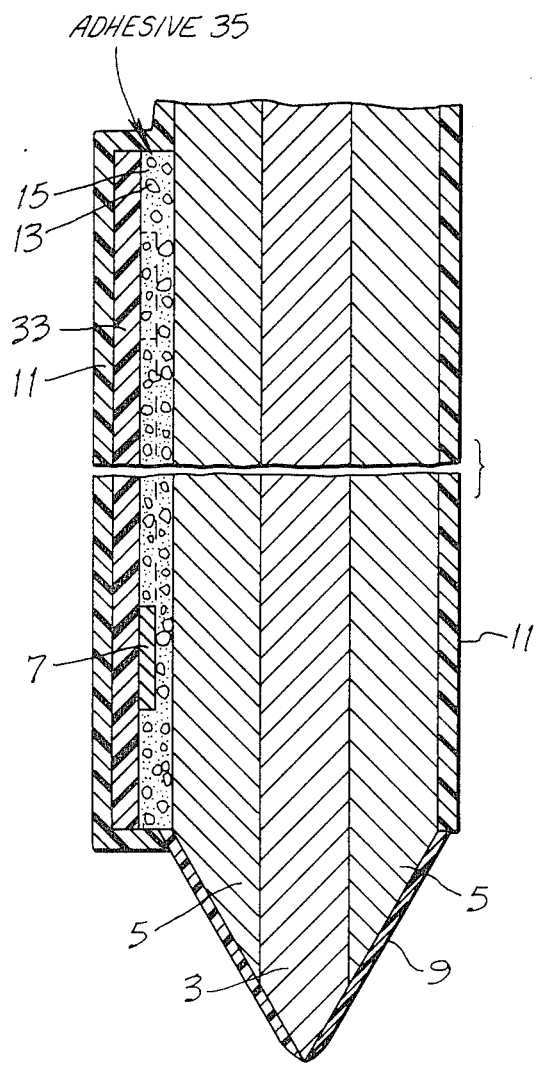

In a preferred embodiment, and as seen for example in FIG. 4, the thickness of the steel substrate 3 is approximately 6 mils and the thickness of the copper composition 5 is approximately 6 mils. Further, the thickness of the heater means 7 is preferably approximately 0.4 mils, while the thickness of the adhesive 35, i.e., the spacing between the heater means and the copper laminate 5, is preferably about 0.4 mils. The backing material 37 is preferably approximately 2 mils in thickness. Due to the physical parameters regarding heat transfer, the cutting instrument of the present invention allows for the cutting instrument 1 to be maintained at a substantially constant temperature within a predetermined range of preferably between about 100 degrees C. and about 300 degrees C.

Figure 2:
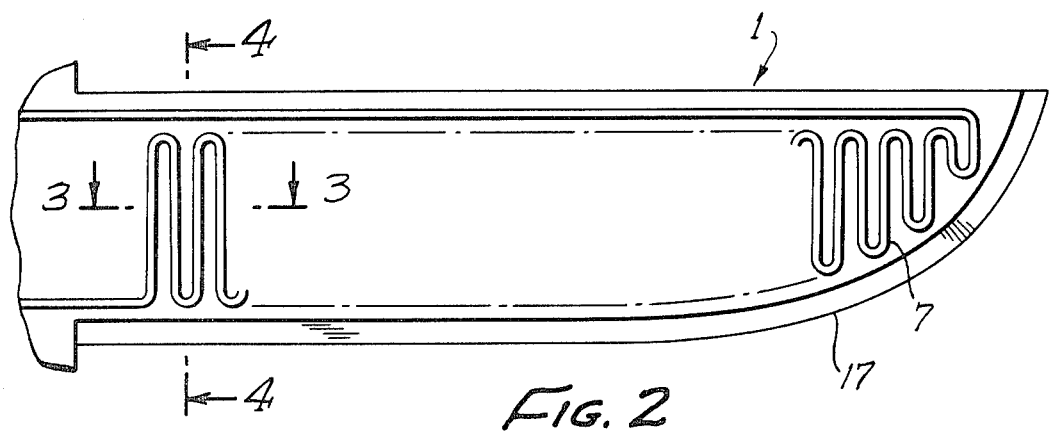
FIG. 2 is a partial pictorial view illustrating the subject matter of this invention.
Figure 3:
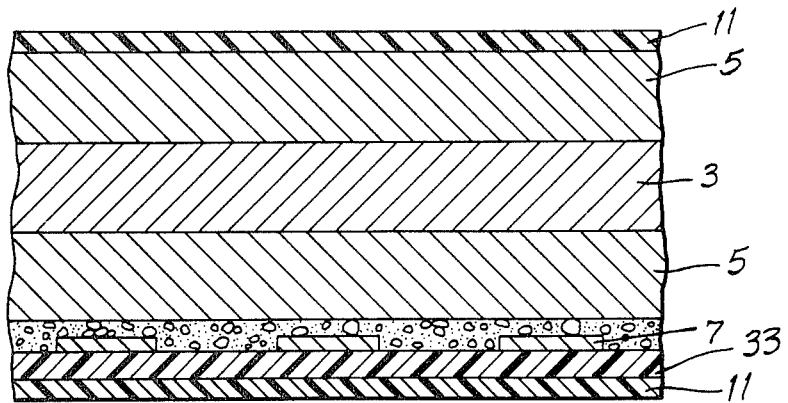
FIGS. 3 and 4 are cross-section views taken about 3—3 and 4—4 of FIG. 2.

As can be seen from FIG. 2, the heater means 7 covers substantially the entire area of one of the flat face portions of the blade adjacent the cutting edge thereby providing continuous heating to the entire cutting portion of the blade. As also can be seen from FIG. 2 and FIG. 4, the width of the copper strip heater means 7 is very small as compared to the width of the blade (both widths being measured in the direction of the section line 4—4).

What is claimed is:

1. A surgical cutting blade adapted to be heated to a predetermined temperature within a predetermined temperature range to provide simultaneous hemostasis during surgery to control bleeding, said cutting blade comprising a metallic member having a pair of opposed flat face portions and a tapered cutting edge portion disposed therebetween along one edge of the member, a heating structure secured to one of the flat face portions substantially throughout the length of the member having said cutting edge thereon for heating said length of the member thoroughly including the cutting edge thereof, said heating structure comprising an elongate strip of conductive material having a thickness in the order of 0.4 mils secured over substantially all of the area of said one flat face portion along said length of the member and being formed in a very narrow width relative to the width of the member, an adhesive directly securing said conductive strip to said one face portion while spacing it from said face portion, said adhesive having thermally conductive and electrically insulative properties, and electrical leads directly connected to said conductive material strip and directed away from the end of the member containing said cutting edge for connecting the strip to an external power source.

2. A surgical cutting blade according to claim 1 wherein said adhesive includes a particulate filler material including particles having a diameter identical to the spacing of the conductive strip and the face portion of the metallic member so as to serve as the spacing means, said filler material having thermally conductive and electrically insulative properties.

3. A surgical cutting blade according to claim 1 including a backing strip of electrically insulative material secured to said heating structure on the side thereof opposite to the side which is adhesively secured to said one flat face portion of said metallic member.

4. A surgical cutting blade according to claim 1 wherein said metallic member is comprised of a copper-steel laminate with the copper layer forming said one flat face portion to which the heating structure is secured.

5. A surgical cutting blade according to claim 1 wherein said metallic member is comprised of a copper steel laminate with both of said flat face portions being formed of copper layers and with a steel substrate extending between the copper layers and including at least the cutting tip portion of said cutting edge.

* * * * *